(12) United States Patent
Staggers et al.

(10) Patent No.: US 12,193,591 B2
(45) Date of Patent: Jan. 14, 2025

(54) HOOKLESS SHOWER CURTAIN WITH SEAMLESS SNAP-ON LINER

(71) Applicants: Rundu Staggers, Norcross, GA (US); Lisa Davis, Norcross, GA (US)

(72) Inventors: Rundu Staggers, Norcross, GA (US); Lisa Davis, Norcross, GA (US)

( * ) Notice: Subject to any disclaimer, the term of this patent is extended or adjusted under 35 U.S.C. 154(b) by 0 days.

(21) Appl. No.: 17/505,615

(22) Filed: Oct. 19, 2021

(65) Prior Publication Data

US 2022/0175168 A1 Jun. 9, 2022

Related U.S. Application Data

(60) Provisional application No. 63/121,910, filed on Dec. 5, 2020.

(51) Int. Cl.
| | |
|---|---|
| *A47H 13/02* | (2006.01) |
| *A47K 3/38* | (2006.01) |
| *A61G 10/00* | (2006.01) |
| *A61G 10/02* | (2006.01) |
| *A61L 9/16* | (2006.01) |
| *A61M 16/10* | (2006.01) |

(52) U.S. Cl.
CPC .............. *A47H 13/02* (2013.01); *A47K 3/38* (2013.01); *A61G 10/005* (2013.01); *A61G 10/023* (2013.01); *A61M 16/105* (2013.01); *A61G 2200/32* (2013.01); *A61L 9/16* (2013.01); *A61L 2209/14* (2013.01)

(58) Field of Classification Search
CPC .................................. A47K 3/38; A47H 13/02
See application file for complete search history.

(56) References Cited

U.S. PATENT DOCUMENTS

| | | | | |
|---|---|---|---|---|
| 2,840,155 | A * | 6/1958 | Stern | A47K 3/38 |
| | | | | D6/578 |
| 5,186,232 | A * | 2/1993 | Zahner | A47H 23/10 |
| | | | | 160/390 |
| 6,038,749 | A * | 3/2000 | Eberhardt | A47H 13/16 |
| | | | | 160/124 |
| 7,296,609 | B2 * | 11/2007 | Zahner | E06B 9/38 |
| | | | | 160/390 |
| 2009/0272502 | A1 * | 11/2009 | Brown | A47K 3/38 |
| | | | | 24/591.1 |
| 2017/0086616 | A1 * | 3/2017 | Hickey | A47H 23/02 |

* cited by examiner

*Primary Examiner* — Janie M Loeppke
(74) *Attorney, Agent, or Firm* — Charlena Thorpe, Esq.; Incorporating Innovation LLC

(57) ABSTRACT

In some implementations, a hookless shower curtain with seamless snap-on liner ("seamless liner shower curtain") comprises a curtain and an attachable (e.g., snap-on) liner. In some implementations, a method of using the seamless liner shower curtain comprises attaching the liner to the curtain and using the seamless liner shower curtain as a shower curtain.

2 Claims, 9 Drawing Sheets

HOOKLESS SHOWER CURTAIN WITH SEAMLESS SNAP-ON LINER

CROSS REFERENCE TO RELATED APPLICATION

This application claims the benefit of U.S. patent application Ser. No. 63/121,910, which was filed on Oct. 19, 2020, and is incorporated herein by reference in its entirety.

TECHNICAL FIELD

This disclosure relates to implementations of a hookless shower curtain with seamless snap-on liner.

BACKGROUND

As shown in FIGS. 1A-1F, existing hookless shower curtains have a snap-on liner that is positioned beneath a sheer portion or panel on the upper part of the shower curtain. FIGS. 1A, 1C, and 1E illustrate the outer side of an existing hookless shower curtain. FIGS. 1B, 1D, and 1F illustrate the inner side of an existing hookless shower curtain showing the snap-on liner.

As shown in FIGS. 1B, 1D, and 1F, the snap-on liner attaches about one-fourth (¼) of the length down from the upper part of the existing hookless shower curtain and exposes the sheer portion. As shown in FIGS. 1A, 1C, and 1E, a seam is visible on the outer side of the existing hookless shower curtain where the liner snaps onto the existing hookless shower curtain. This unsightly seam, as well as the exposed sheer panel, can interfere with the design or other appearance of the existing hookless shower curtain or other suitable shower curtain.

DETAILED DESCRIPTION

Implementations of a hookless shower curtain with seamless snap-on liner ("seamless liner shower curtain") are provided. In some implementations, the seamless liner shower curtain comprises a curtain and an attachable (e.g., snap-on) liner.

In some implementations, the seamless liner shower curtain is configured such that a design, image, or other appearance of the curtain is not interfered with or otherwise affected by the attached liner, such as by causing a seam or exposing a sheer portion or panel.

In some implementations, a method of using the seamless liner shower curtain comprises attaching the liner to the curtain and using the seamless liner shower curtain as a shower curtain.

Figure 1A:
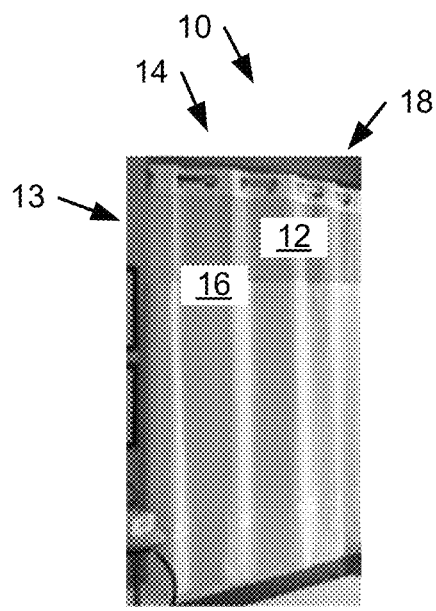
FIGS. 1A-1F illustrate an example existing hookless shower curtain with a snap-on liner.
Figure 1B:
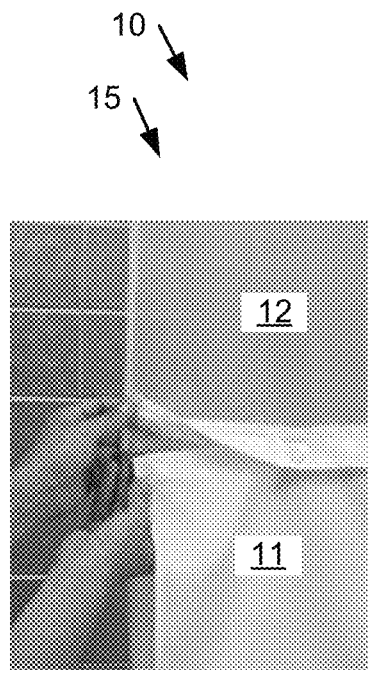
Figures 1C, 1D:
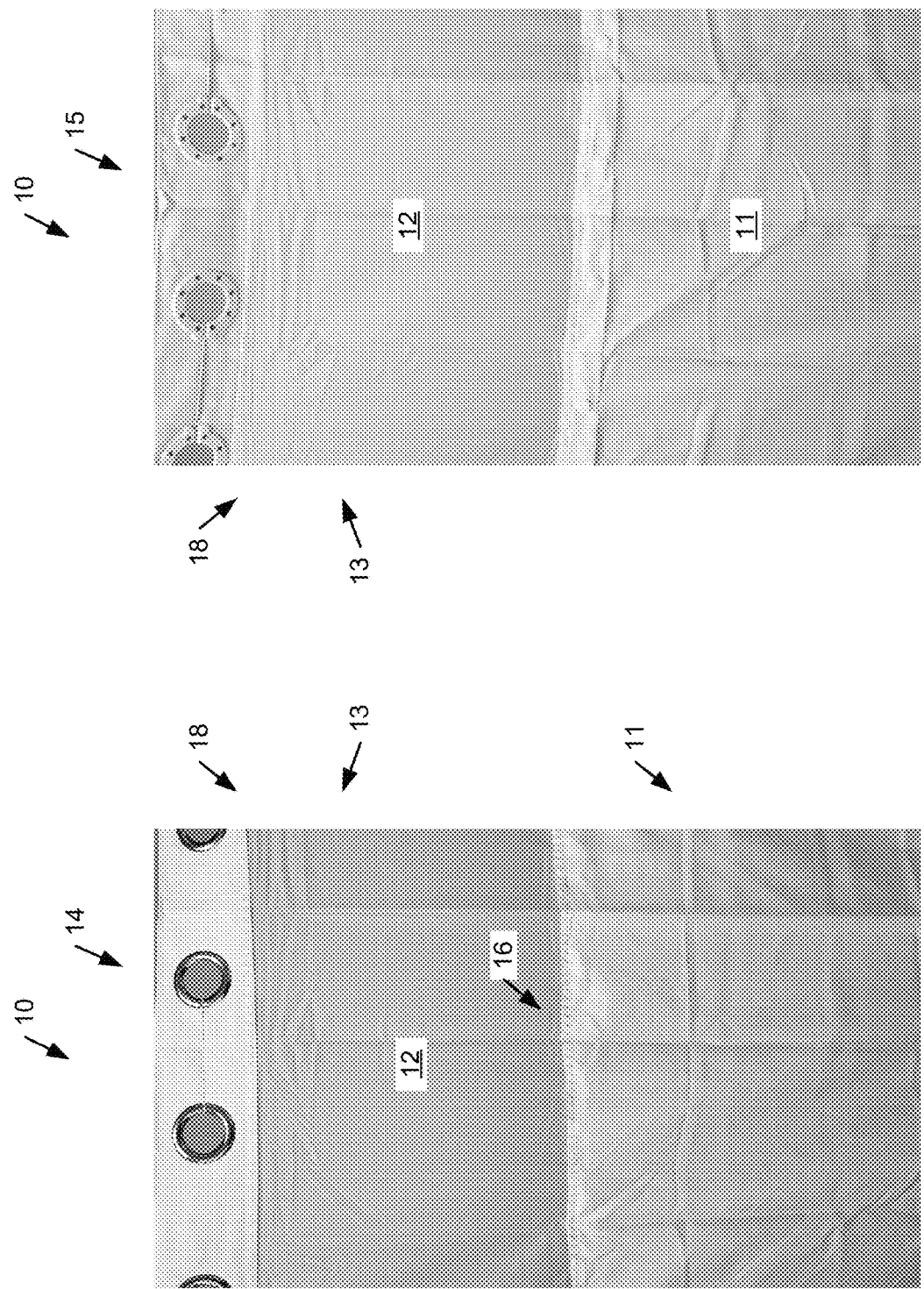
Figure 1F:
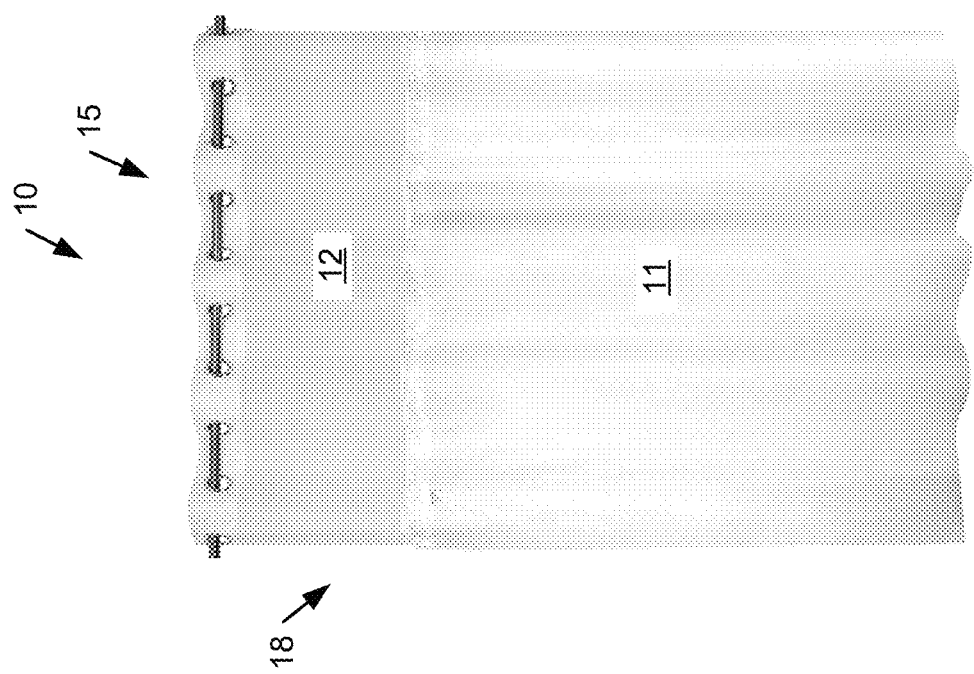
Figure 1E:
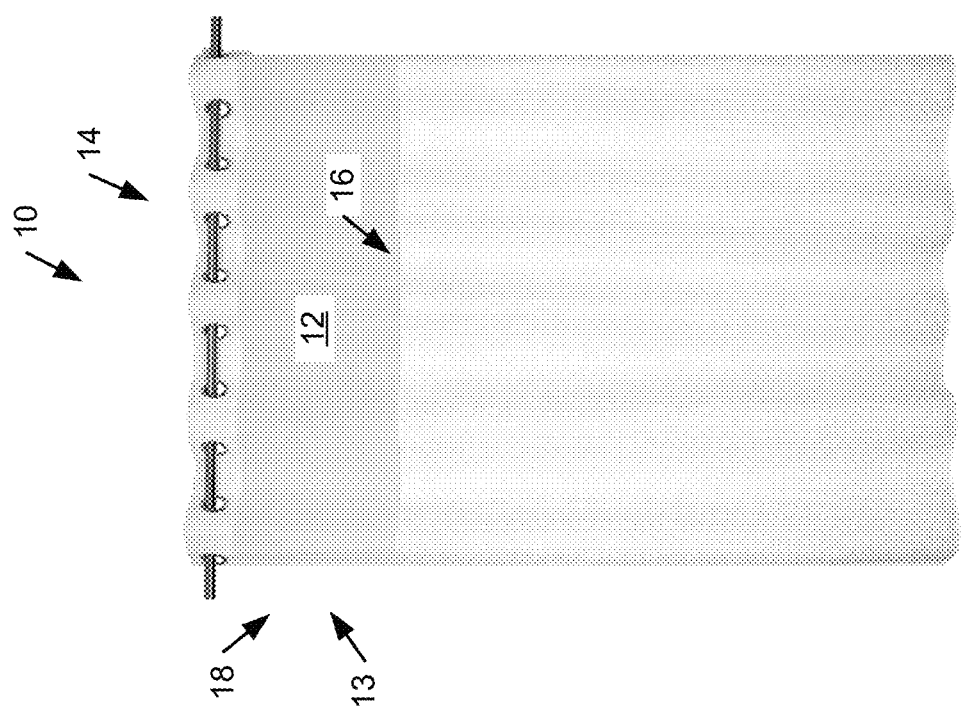

FIGS. 1A-1F illustrate an example existing hookless shower curtain with snap-on liner 10. As shown in FIGS. 1A-1F, such existing hookless shower curtains 10 have a snap-on liner 11 that is positioned beneath a sheer portion or panel 12 on the upper part 13 of the curtain part 18 of the shower curtain 10. FIGS. 1A, 1C, and 1E illustrate the outer side 14 of an existing hookless shower curtain 10. FIGS. 1B, 1D, and 1F illustrate the inner side 15 of existing hookless shower curtain showing the snap-on liner 11.

As shown in FIGS. 1B, 1D, and 1F, the snap-on liner 11 attaches about one-fourth (¼) of the length down from the upper part 13 of the curtain part 18 of the shower curtain 10 and exposes the sheer portion 12. As shown in FIGS. 1A, 1C, and 1E, a seam 16 is visible on the outer side 14 of the existing hookless shower curtain 10 where the liner 11 snaps onto the curtain part 18. This unsightly seam 16, as well as the exposed sheer portion 12, can interfere with the design or other appearance of the existing hookless shower curtain 10 or other suitable shower curtain.

Figure 2B:
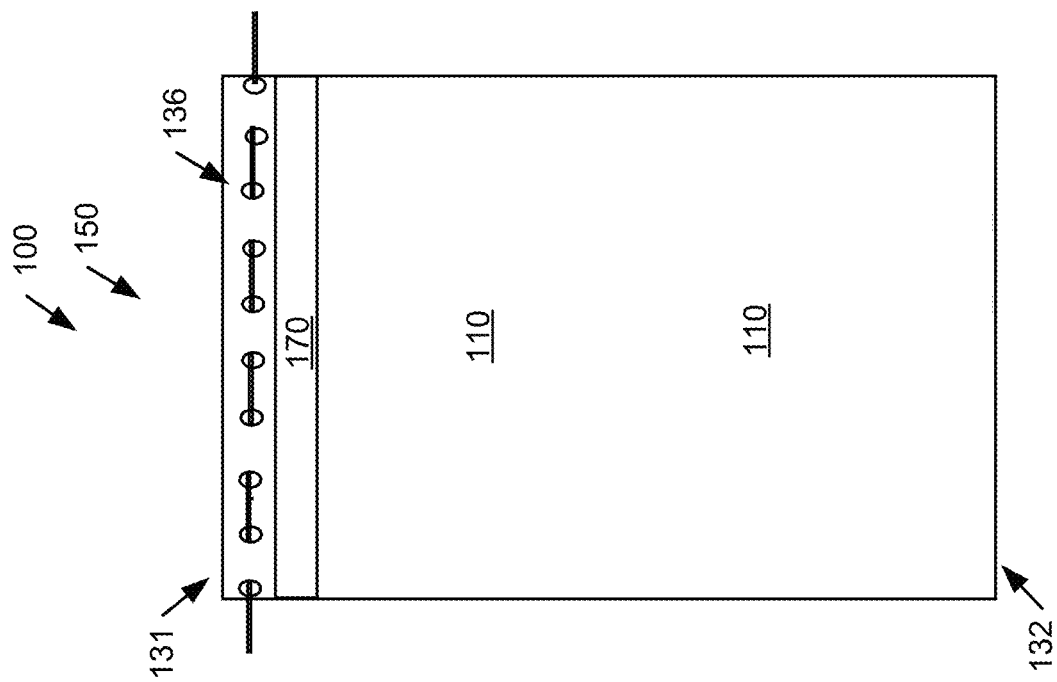
FIGS. 2A-2H illustrate implementations of an example hookless shower curtain with seamless snap-on liner according to the present disclosure.
Figure 2A:
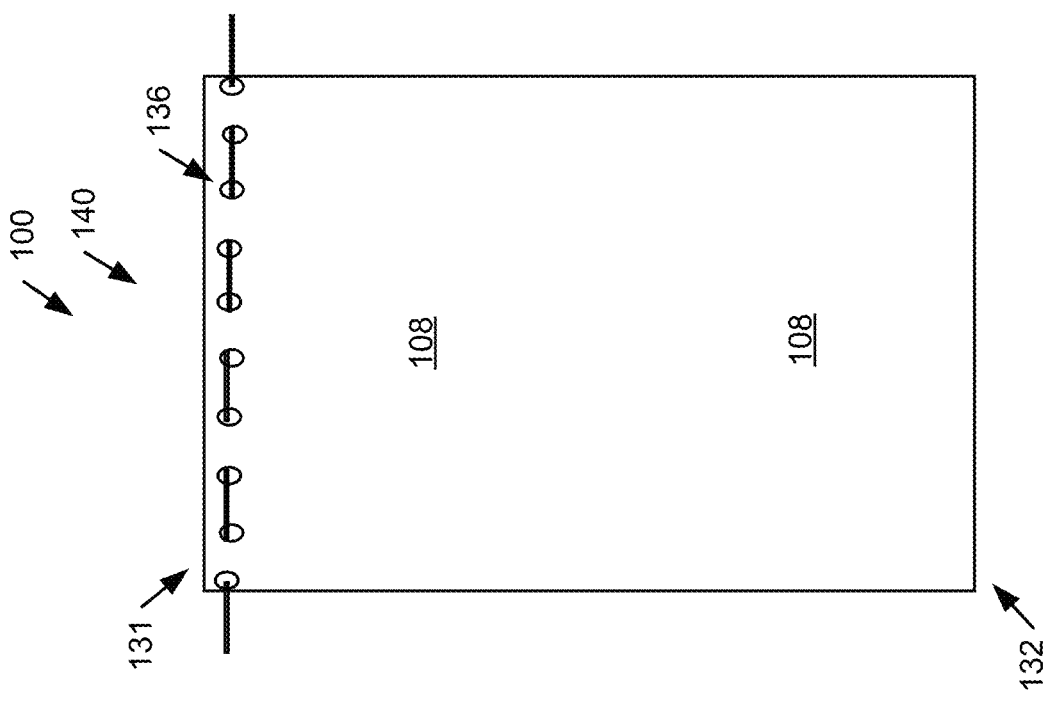
Figure 2C:
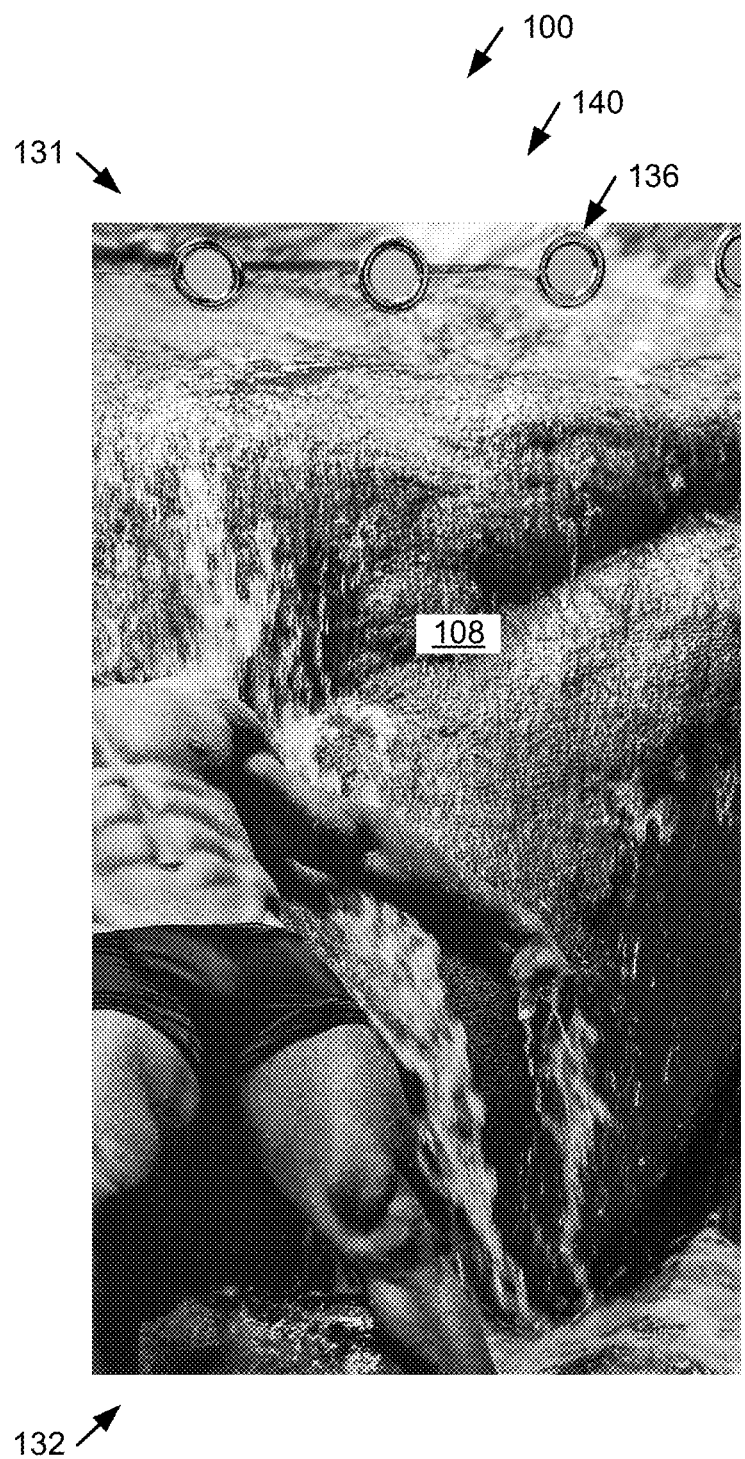

FIGS. 2A-2H illustrate implementations of an example hookless shower curtain with seamless snap-on liner ("seamless liner shower curtain") 100 according to the present disclosure. FIGS. 2C-2H illustrate the seamless liner shower curtain 100 with an example design or image; FIGS. 2A and 2B illustrate the seamless liner shower curtain 100 without the example design or image to show further detail of the seamless liner shower curtain 100.

Figure 2D:
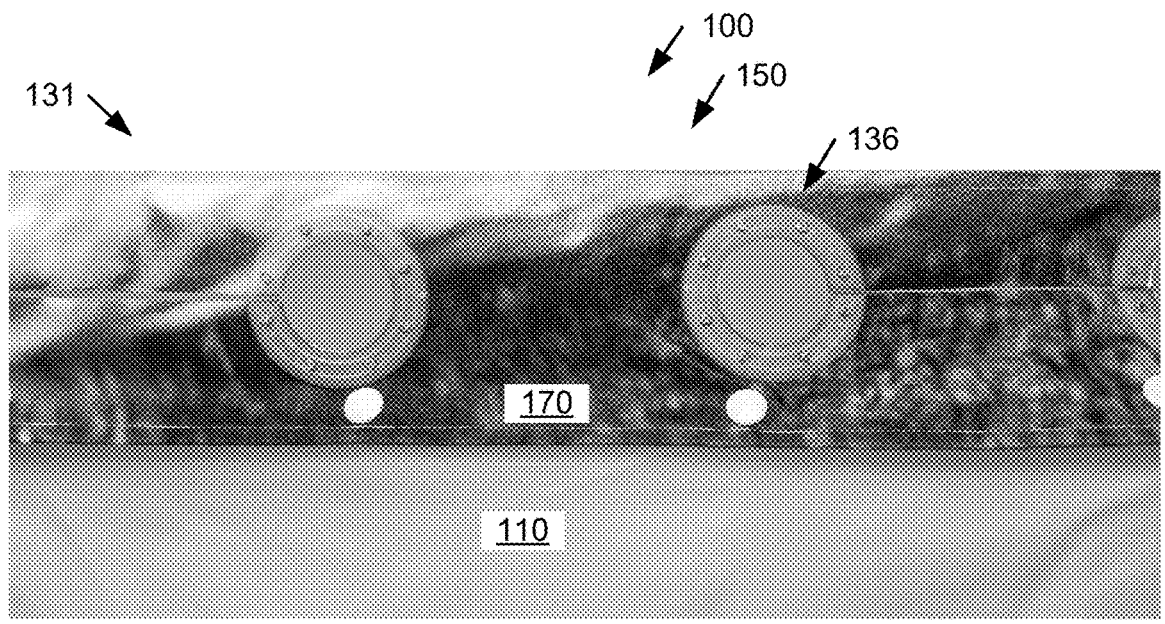
Figure 2E:
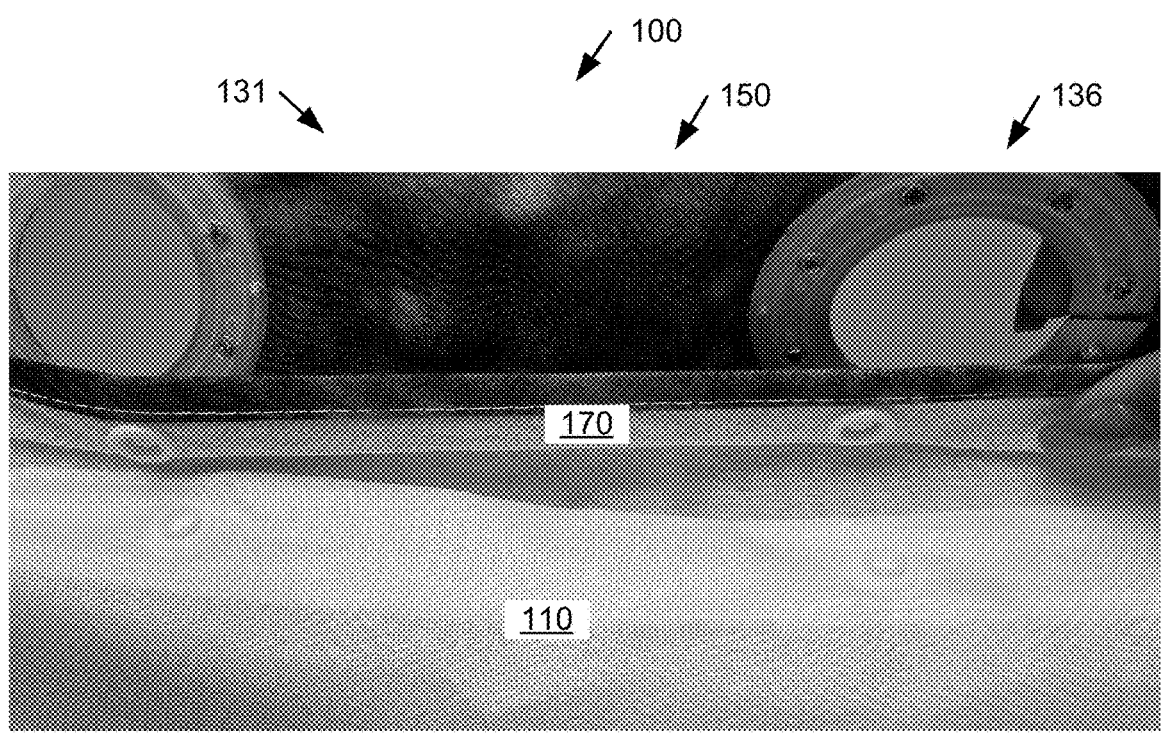
Figure 2F:
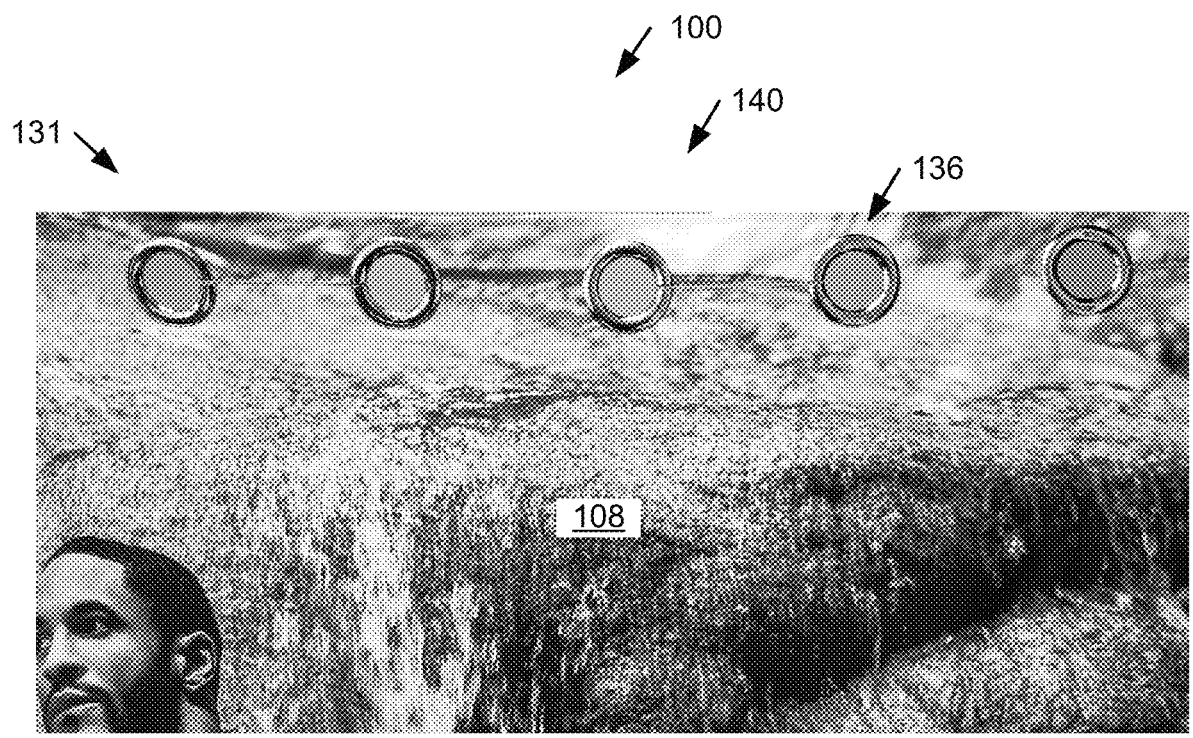
Figure 2G:
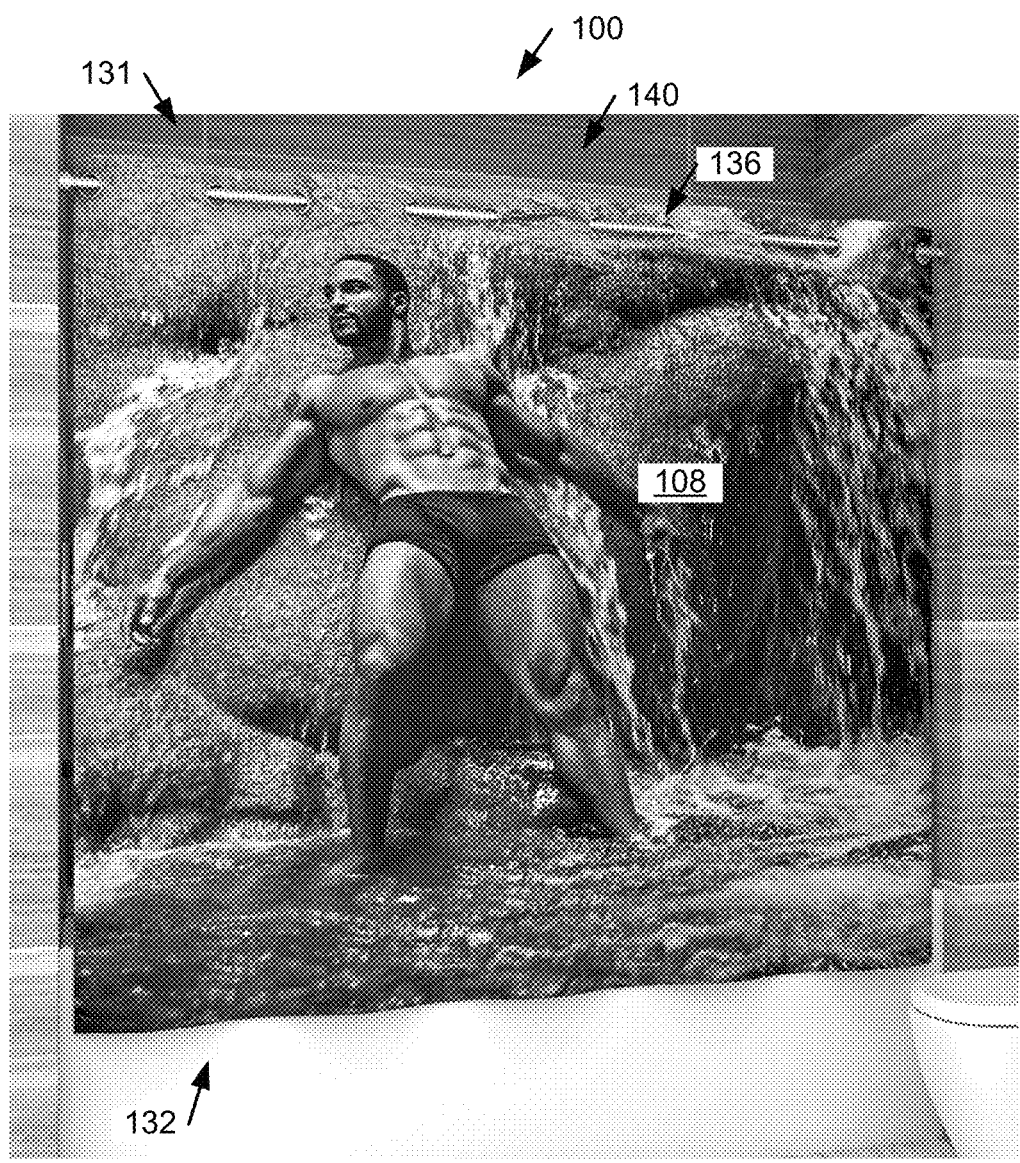
Figure 2H:
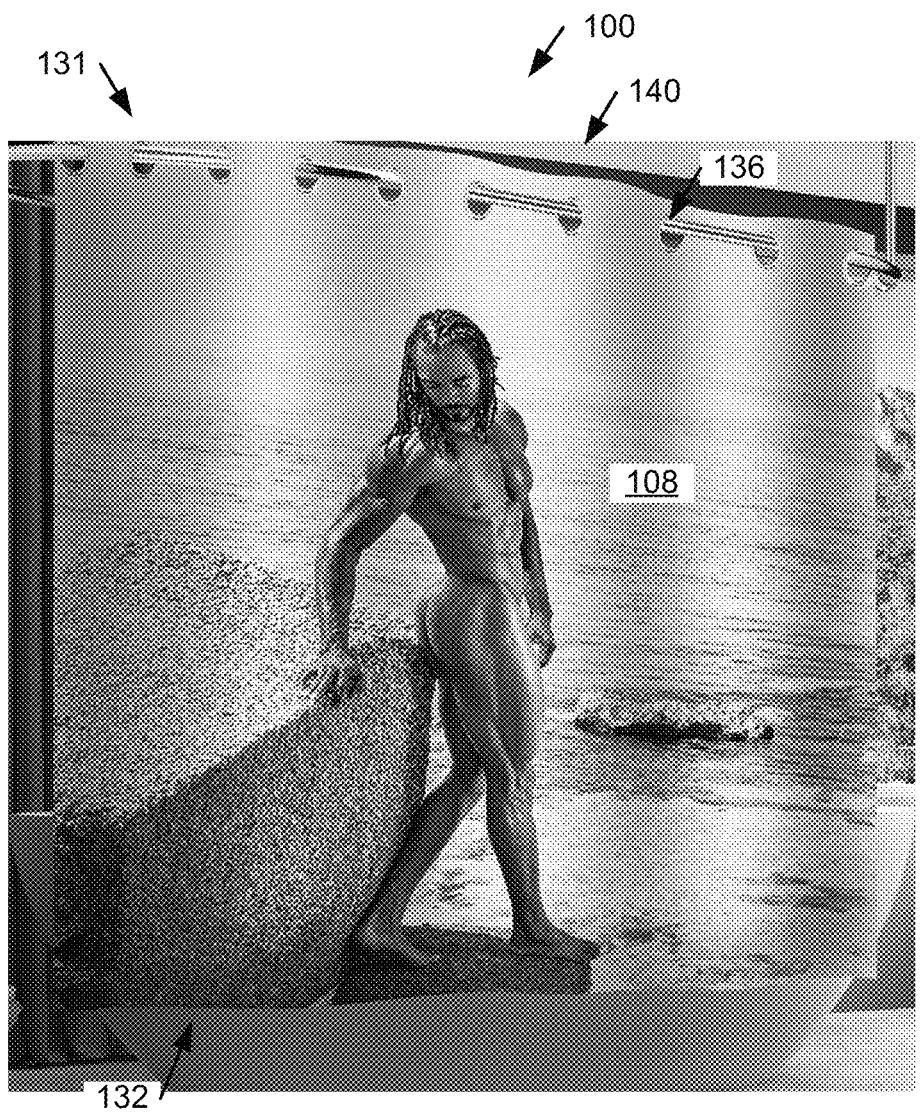

Furthermore, FIGS. 2A, 2C, and 2F-2H illustrate the outer side 140 of the seamless liner shower curtain 100, and FIGS. 2B, 2D, and 2E illustrate the inner side 150 of the seamless liner shower curtain 100.

As shown in FIGS. 2A and 2B, in some implementations, the seamless liner shower curtain 100 comprises a curtain 108 and an attachable (e.g., snap-on) liner 110. In some implementations, the curtain 108 and liner 110 are generally similar to the above described curtain 18 and liner 11 of FIGS. 1A-1F except as described below.

As shown in FIGS. 2B, 2D, and 2E, in contrast to the curtain 18 of FIGS. 1A-1F, in some implementations, the curtain 108 comprises a liner attachment point 170 that is positioned near or adjacent the rings 136 and the upper side 131 of the curtain 108. Furthermore, as shown in FIG. 2B, in some implementations, the liner 110 is configured to extend from the attachment point 170 to or near the lower side 132 of the curtain 108.

As shown in FIGS. 2D and 2E, in some implementations, the material forming the curtain 108 folds over at the upper side 131 and extends back toward the lower side 132 in a hem-like configuration wherein the attachment portion 170 (such as snaps or other attachment mechanism) is attached adjacent (e.g., at or near) the edge or end of the material (e.g., below the upper side 131 and/or the rings 136). Thereby, in some implementations, the attachment portion 170 is not attached to a portion of the curtain 108 that is visible from the outer side 140 of the curtain 108.

As shown in FIGS. 2D and 2E, in some implementations, the folded or hem-like configuration of the material forming the curtain 108 may be held together or otherwise secured by the rings 136. In some implementations, the folded or hem-like configuration of the material forming the curtain 108 may be held together or otherwise secured by stitching or other suitable way (e.g., adhesive). In some implementations, the portion of the curtain extending from the upper side 131 toward the lower side 132 forming the folded or hem-like configuration may comprise a separate piece of material attached to the other material forming the curtain 108, wherein the attachment is not visible from the outer side 140 of the curtain 108.

In this way, as shown in FIGS. 2A, 2C, 2G, and 2H, in some implementations, the seamless liner shower curtain 100 does not have a visible seam for the attachment portion 170 for the liner 110 like the above described seam 16 of FIGS. 1A-1F. Furthermore, in this way, in some implementations, the seamless liner shower curtain 100 does not have an exposed sheer portion or panel like the above described sheer portion 12 of FIGS. 1A-1F. Thereby, in contrast to the curtain 18 of FIGS. 1A-1F, in some implementations, the design, image, or other appearance of the curtain 108 is not interfered with or otherwise affected by the liner 110 attached to the curtain 108 for the seamless liner shower curtain 100.

In addition to the above description, in some implementations, the seamless liner shower curtain 100 does not have an exposed sheer portion or panel because the curtain 108 is not sheer (e.g., because of the material, an image on the curtain 108, etc.). Alternately, in some implementations, the seamless liner shower curtain 100 does not have an exposed sheer portion or panel because the liner 110 attached to the curtain 108 extends the visible length and width of the curtain 108 along the inner side 150 of the curtain 108 (e.g., for a sheer or otherwise translucent curtain 108).

As described above, in some implementations, the liner 110 and/or the attachment point 170 may comprise a snap attachment mechanism. In some implementations, the liner 110 and/or the attachment point 170 may comprise any other suitable attachment mechanism, such as a hook and loop attachment mechanism, an interlocking component (e.g., groove and ridge) attachment mechanism, a button attachment mechanism, a zipper attachment mechanism, or any other suitable attachment technology existing or developed in the future.

In some implementations, the curtain 108 and/or the liner 110 may further comprise weights or weighted magnets positioned at or adjacent to the lower side 132 of the seamless liner shower curtain 100.

In some implementations, the seamless liner shower curtain 100 may further comprise any other suitable components to provide the features of the seamless liner shower curtain 100 described herein.

In some implementations, the seamless liner shower curtain 100 is configured, in accordance with the above described features, to provide a hookless shower curtain 108 with a seamless attached (e.g., snap-on) liner 110.

In some implementations, the seamless liner shower curtain 100 is configured such that a design, image, or other appearance of the curtain 108 is not interfered with or otherwise affected by the attached liner 110, such as by causing a seam or exposing a sheer portion or panel.

In some implementations, the seamless liner shower curtain 100 may be configured to provide any other suitable shower curtain with a seamless attached liner having the features described herein.

In some implementations, the seamless liner shower curtain 100 comprises any suitable dimensions. For example, in some implementations, the curtain 108 may be 74 inches long and 71 inches wide. In some implementations, the curtain 108 may be less than or greater than 74 inches long and/or less than or greater than 71 inches wide.

Similarly, in some implementations, the liner 110 may be 68 inches long and 71 inches wide. In some implementations, the liner 110 may be less than or greater than 68 inches long and/or less than or greater than 71 inches wide.

In some implementations, the seamless liner shower curtain 100 is composed of any suitable materials. For example, in some implementations, the seamless liner shower curtain 100 is composed of one or more forms of a polyester material.

In some implementations, the seamless liner shower curtain 100 can have any suitable appearance, such as the example appearances shown in FIGS. 2A-2H. For example, in some implementations, the curtain 108 comprises a design or image.

In some implementations, an example method of using the seamless liner shower curtain 100, with respect to the above-described figures, comprises attaching (e.g., snapping) the liner 110 to the curtain 108 at the attachment point 170 to form the seamless liner shower curtain 100. In some implementations, the liner 110 is attached such that a design, image, or other appearance of the curtain 108 is not interfered with or otherwise affected by the attached liner 110, such as by causing a seam or exposing a sheer portion or panel.

In some implementations, the method comprises installing the seamless liner shower curtain 100 in a shower area, such as a shower stall or bathtub. In some implementations, the seamless liner shower curtain 100 is installed by attaching the rings 136 to a shower bar or similar installation component.

In some implementations, the method comprises using the seamless liner shower curtain 100 as a shower curtain. For example, in some implementations, the seamless liner shower curtain 100 is used to contain water while showering. In some implementations, the seamless liner shower curtain is used to provide a decorative or otherwise desired appearance to a shower area.

In some implementations, the method may comprise any other suitable use of the seamless liner shower curtain 100.

The figures, including photographs and drawings, comprised herewith may represent one or more implementations of the hookless shower curtain with seamless snap-on liner.

Details shown in the figures, such as dimensions, descriptions, etc., are exemplary, and there may be implementations of other suitable details according to the present disclosure.

Reference throughout this specification to "an embodiment" or "implementation" or words of similar import means that a particular described feature, structure, or characteristic is comprised in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations may be depicted in the drawings in a particular order, this should not be understood as requiring that such operations be performed in the particular order shown or in sequential order, or that all illustrated operations be performed, to achieve desirable results.

The invention claimed is:

1. An article of manufacture comprising:
   a curtain portion formed from a first material extending lengthwise from a first edge to a second edge and extending widthwise from a third edge to a fourth edge, wherein the first material has an outer surface on an outer side and an inner surface on an inner side, wherein an upper portion of the first material including the first edge is folded toward the inner side such that the outer surface of the folded upper portion of the first material including the first edge is positioned on the inner side of the first material thereby forming a folded portion extending lengthwise from an outer edge formed from the fold to the first edge positioned behind a corresponding portion of the first material;

wherein a portion of the folded portion is permanently secured to the corresponding portion of the first material wherein the first edge and a portion of the first material adjacent to the first edge extending from the third edge to the fourth edge of the first material is not attached to the corresponding portion of the first material thereby forming a free edge on the inner side of the first material behind the first material extending from the third edge to the fourth edge of the first material such that the first material does not have a visible seam formed by the folded portion on the outer surface of the first material;

wherein a portion of the folded portion and the corresponding portion of the first material comprises openings extending therethrough and slits extending thereto and between openings thereby forming a hookless shower curtain; and wherein the folded portion is permanently secured to the corresponding portion of the first material using an attachment mechanism surrounding the openings extending through the folded portion and the corresponding portion of the first material;

and a liner portion formed from a second material extending lengthwise from a first edge to a second edge and extending widthwise from a third edge to a fourth edge wherein a portion of the second material adjacent to the first edge of the second material and extending from the third edge to the fourth edge of the second material is configured to removably attach to the free edge on the inner side of the first material behind the first material.

2. An article of manufacture comprising:

a curtain portion formed from a first material extending lengthwise from a first edge to a second edge and extending widthwise from a third edge to a fourth edge, wherein the first material has an outer surface on an outer side and an inner surface on an inner side, wherein an upper portion of the first material including the first edge is folded toward the inner side such that the outer surface of the folded upper portion of the first material including the first edge is positioned on the inner side of the first material thereby forming a folded portion extending lengthwise from an outer edge formed from the fold to the first edge positioned behind a corresponding portion of the first material;

wherein a portion of the folded portion is secured to the corresponding portion of the first material using a first attachment mechanism wherein the first edge and a portion of the first material adjacent to the first edge extending from the third edge to the fourth edge of the first material is not attached to the corresponding portion of the first material thereby forming a free edge on the inner side of the first material behind the first material extending from the third edge to the fourth edge of the first material such that the first material does not have a visible seam formed by the folded portion on the outer surface of the first material;

wherein a portion of the folded portion and the corresponding portion of the first material comprises openings extending therethrough and slits extending thereto and between openings thereby forming a hookless shower curtain; and wherein the folded portion is secured to the corresponding portion of the first material using the first attachment mechanism wherein the first attachment mechanism surrounds the openings extending through the folded portion and the corresponding portion of the first material;

and a liner portion formed from a second material extending lengthwise from a first edge to a second edge and extending widthwise from a third edge to a fourth edge wherein a portion of the second material adjacent to the first edge of the second material and extending from the third edge to the fourth edge of the second material is configured to removably attach to the free edge on the inner side of the first material behind the first material using a second attachment mechanism wherein the first attachment mechanism and the second attachment mechanism are different.

\* \* \* \* \*